(12) United States Patent
Farr et al.

(10) Patent No.: US 8,057,481 B2
(45) Date of Patent: Nov. 15, 2011

(54) SYSTEM AND METHOD FOR PROVIDING SURGICAL ACCESS TO A SPINE

(75) Inventors: Morteza M. Farr, Manteca, CA (US); Joshua A. Butters, Chandler, AZ (US); T. Wade Fallin, Hyde Park, UT (US)

(73) Assignee: Innovative Spine, LLC, Covis, CA (US)

( * ) Notice: Subject to any disclaimer, the term of this patent is extended or adjusted under 35 U.S.C. 154(b) by 1141 days.

(21) Appl. No.: 11/831,728

(22) Filed: Jul. 31, 2007

(65) Prior Publication Data

US 2009/0012568 A1  Jan. 8, 2009

Related U.S. Application Data

(60) Provisional application No. 60/856,682, filed on Nov. 3, 2006.

(51) Int. Cl.
*A61B 17/58* (2006.01)
*A61B 17/60* (2006.01)
*A61F 2/00* (2006.01)

(52) U.S. Cl. ............... 606/99; 606/96; 606/279

(58) Field of Classification Search ............ 606/279, 606/99, 914, 86 A
See application file for complete search history.

(56) References Cited

U.S. PATENT DOCUMENTS

| 3,090,386 A | 5/1963 | Curtis |
| 3,556,103 A | 1/1971 | Calhoun et al. |
| 3,570,498 A | 3/1971 | Weighton |
| 3,608,539 A | 9/1971 | Miller |
| 3,941,127 A | 3/1976 | Froning |
| 3,946,740 A | 3/1976 | Bassett |
| 3,948,274 A | 4/1976 | Zeldman et al. |
| 4,265,231 A | 5/1981 | Scheller, Jr. et al. |
| 4,312,337 A | 1/1982 | Donohue |
| 4,335,715 A | 6/1982 | Kirkley |

(Continued)

FOREIGN PATENT DOCUMENTS

WO  WO 2005/032358 A2  4/2005
(Continued)

OTHER PUBLICATIONS

International Search Report and Written Opinion from Related PCT Application No. PCT/US2009/031751, Aug. 26, 2009 (13 pgs).

(Continued)

*Primary Examiner* — Thomas C. Barrett
*Assistant Examiner* — Andrew Yang
(74) *Attorney, Agent, or Firm* — GSS Law Group

(57) ABSTRACT

A system for accessing a spine from a curved postero-lateral approach may include a curved cannula positioned along a curved path from an opening in the skin to a location proximate the spine. A guide member may be first inserted to establish the path between the tissues and fascia, and one or more intermediate cannulas may be temporarily inserted over the guide member to dilate the tissues prior to insertion of the main cannula. An interbody device may be implanted in an intervertebral space through the cannula. The system may include a guide bar removably coupled to a targeting post. The targeting post may be inserted adjacent the spine to provide a target, and the guide bar may be removably attached to the guide member, to guide it along the path to the target location. An external support arm may be secured to any other component of the system.

29 Claims, 15 Drawing Sheets

U.S. PATENT DOCUMENTS

| | | |
|---|---|---|
| 4,449,532 A | 5/1984 | Storz |
| 4,511,356 A | 4/1985 | Froning et al. |
| 4,541,423 A | 9/1985 | Barber |
| 4,545,374 A | 10/1985 | Jacobson |
| 4,573,448 A | 3/1986 | Kambin |
| 4,598,705 A | 7/1986 | Lichtenberger |
| 4,686,972 A | 8/1987 | Kurland |
| 4,722,331 A | 2/1988 | Fox |
| 4,756,708 A | 7/1988 | Martin |
| 4,862,891 A | 9/1989 | Smith |
| 4,863,430 A | 9/1989 | Klyce et al. |
| 4,883,048 A | 11/1989 | Purnell et al. |
| 4,926,860 A | 5/1990 | Stice et al. |
| 4,957,495 A | 9/1990 | Kluger |
| 5,080,662 A | 1/1992 | Paul |
| 5,163,940 A | 11/1992 | Bourque |
| 5,242,444 A | 9/1993 | MacMillan |
| 5,300,077 A | 4/1994 | Howell |
| 5,330,468 A | 7/1994 | Burkhart |
| 5,334,205 A | 8/1994 | Cain |
| 5,458,602 A | 10/1995 | Goble et al. |
| 5,601,562 A | 2/1997 | Wolf et al. |
| 5,613,971 A | 3/1997 | Lower et al. |
| 5,725,532 A | 3/1998 | Shoemaker |
| 5,741,261 A | 4/1998 | Moskovitz et al. |
| 5,772,661 A | 6/1998 | Michelson |
| 5,860,973 A | 1/1999 | Michelson |
| 5,891,147 A | 4/1999 | Moskovitz et al. |
| 6,042,582 A | 3/2000 | Ray |
| 6,080,155 A | 6/2000 | Michelson |
| 6,083,225 A | 7/2000 | Winslow |
| 6,096,038 A | 8/2000 | Michelson |
| 6,162,170 A | 12/2000 | Foley et al. |
| 6,224,603 B1 | 5/2001 | Marino |
| 6,226,548 B1 | 5/2001 | Foley et al. |
| 6,245,072 B1 | 6/2001 | Zdeblick et al. |
| 6,270,498 B1 | 8/2001 | Michelson |
| 6,419,678 B1 | 7/2002 | Asfora |
| 6,530,929 B1 | 3/2003 | Justis et al. |
| 6,547,795 B2 | 4/2003 | Schneiderman |
| 6,564,078 B1 * | 5/2003 | Marino et al. ............. 600/373 |
| 6,575,899 B1 | 6/2003 | Foley et al. |
| 6,592,559 B1 | 7/2003 | Pakter et al. |
| 6,604,003 B2 | 8/2003 | Fredricks et al. |
| 6,638,276 B2 | 10/2003 | Sharkey et al. |
| 6,669,698 B1 | 12/2003 | Tromanhauser et al. |
| 6,733,496 B2 | 5/2004 | Sharkey et al. |
| 6,740,090 B1 | 5/2004 | Cragg et al. |
| 6,764,491 B2 | 7/2004 | Frey et al. |
| 6,790,210 B1 | 9/2004 | Cragg et al. |
| 6,796,983 B1 | 9/2004 | Zucherman et al. ............ 606/61 |
| 6,824,565 B2 | 11/2004 | Muhanna et al. |
| 6,830,570 B1 | 12/2004 | Frey et al. |
| 6,875,219 B2 | 4/2005 | Arramon et al. |
| 6,929,606 B2 * | 8/2005 | Ritland ................ 600/201 |
| 6,980,862 B2 | 12/2005 | Fredricks et al. |
| 7,008,422 B2 | 3/2006 | Foley et al. |
| 7,011,660 B2 | 3/2006 | Sherman et al. |
| RE39,133 E | 6/2006 | Clayton et al. |
| 7,060,068 B2 | 6/2006 | Tromanhauser et al. |
| 7,060,073 B2 | 6/2006 | Frey et al. |
| 7,074,226 B2 | 7/2006 | Roehm et al. |
| 2002/0013514 A1 | 1/2002 | Brau |
| 2002/0019637 A1 | 2/2002 | Frey et al. |
| 2002/0065541 A1 | 5/2002 | Fredricks et al. |
| 2002/0091387 A1 | 7/2002 | Hoogland |
| 2002/0156420 A1 | 10/2002 | Anderson et al. |
| 2002/0161368 A1 | 10/2002 | Foley et al. |
| 2002/0165550 A1 | 11/2002 | Frey et al. |
| 2003/0032929 A1 | 2/2003 | McGuckin |
| 2003/0074005 A1 | 4/2003 | Roth et al. |
| 2003/0083688 A1 | 5/2003 | Simonson |
| 2003/0120308 A1 | 6/2003 | Loubens et al. |
| 2003/0191474 A1 | 10/2003 | Cragg et al. |
| 2003/0199871 A1 | 10/2003 | Foley et al. |
| 2003/0208202 A1 | 11/2003 | Falahee |
| 2003/0229347 A1 | 12/2003 | Sherman et al. |
| 2004/0015215 A1 | 1/2004 | Fredricks et al. |
| 2004/0030346 A1 | 2/2004 | Frey et al. |
| 2004/0034351 A1 | 2/2004 | Sherman et al. |
| 2004/0068242 A1 | 4/2004 | McGuckin |
| 2004/0092928 A1 | 5/2004 | Sasso |
| 2004/0106997 A1 | 6/2004 | Lieberson |
| 2004/0117020 A1 | 6/2004 | Frey et al. |
| 2004/0133168 A1 | 7/2004 | Salcudean et al. |
| 2004/0153005 A1 | 8/2004 | Krueger |
| 2004/0162559 A1 | 8/2004 | Arramon et al. |
| 2004/0199168 A1 | 10/2004 | Bertagnoli et al. |
| 2004/0215190 A1 | 10/2004 | Nguyen et al. |
| 2004/0220577 A1 | 11/2004 | Cragg et al. |
| 2005/0021031 A1 | 1/2005 | Foley et al. |
| 2005/0021040 A1 | 1/2005 | Bertagnoli |
| 2005/0137605 A1 | 6/2005 | Assell et al. |
| 2005/0137612 A1 | 6/2005 | Assell et al. |
| 2005/0149035 A1 | 7/2005 | Pimenta et al. |
| 2005/0165405 A1 | 7/2005 | Tsou |
| 2005/0171540 A1 | 8/2005 | Lim et al. |
| 2005/0177239 A1 | 8/2005 | Steinberg |
| 2005/0187543 A1 | 8/2005 | Underwood et al. |
| 2005/0209610 A1 | 9/2005 | Carrison |
| 2005/0256578 A1 | 11/2005 | Blatt et al. |
| 2005/0261773 A1 | 11/2005 | Ferree |
| 2006/0009780 A1 | 1/2006 | Foley et al. |
| 2006/0036241 A1 | 2/2006 | Siegal |
| 2006/0036273 A1 | 2/2006 | Siegal |
| 2006/0052848 A1 | 3/2006 | Fredricks et al. |
| 2006/0064101 A1 | 3/2006 | Arramon |
| 2006/0084977 A1 | 4/2006 | Lieberman |
| 2006/0111714 A1 | 5/2006 | Foley |
| 2006/0111728 A1 | 5/2006 | Abdou |
| 2006/0129101 A1 | 6/2006 | McGuckin, Jr. |
| 2006/0135915 A1 | 6/2006 | Tucker |
| 2006/0135916 A1 | 6/2006 | Tucker |
| 2006/0149278 A1 | 7/2006 | Abdou ......................... 606/90 |
| 2006/0189986 A1 | 8/2006 | Sherman et al. |
| 2006/0195102 A1 | 8/2006 | Malandain |
| 2006/0200129 A1 | 9/2006 | Denti |
| 2006/0200135 A1 | 9/2006 | Sherman et al. |
| 2006/0217806 A1 | 9/2006 | Peterman et al. |
| 2006/0217807 A1 | 9/2006 | Peterman et al. |
| 2006/0229614 A1 | 10/2006 | Foley et al. |
| 2006/0264968 A1 | 11/2006 | Frey et al. |
| 2007/0093689 A1 | 4/2007 | Steinberg |
| 2007/0203497 A1 | 8/2007 | Zucherman et al. |
| 2008/0249531 A1 | 10/2008 | Patterson |

FOREIGN PATENT DOCUMENTS

| | | |
|---|---|---|
| WO | WO 2006/041963 A2 | 4/2006 |
| WO | WO 2006/089085 A2 | 8/2006 |

OTHER PUBLICATIONS

U.S. Appl. No. 60/9000554, filed Feb. 9, 2007, Garcia-Bengochea.

Mazor Surgical Technologies, http://www.mazorst.com/SpineAssist-product.asp 2008 Website.

International Search Report and Written Opinion From Corresponding PCT Application No. PCT/US2007/083625, Aug. 6, 2008 (8 pgs).

* cited by examiner

SYSTEM AND METHOD FOR PROVIDING SURGICAL ACCESS TO A SPINE

CROSS-REFERENCE TO RELATED APPLICATIONS

This application claims the benefit of U.S. Provisional Patent Application No. 60/856,682, filed Nov. 3, 2006, which is entitled METHOD AND APPARATUS FOR SPINAL SURGERY.

BACKGROUND OF THE INVENTION

1. The Field of the Invention

The invention relates to orthopaedics, and more particularly, to systems and methods for providing access to the spine to facilitate various implantation procedures.

2. The Relevant Technology

Many spinal orthopaedic procedures including discectomy, implantation of motion preservation devices, total disk replacement, and implantation of interbody devices require unimpeded access to a targeted portion of the spinal column. A lateral interbody fusion approach requires the patient to be turned mid-process to complete the disc and interbody device procedures. An anterior approach requires the presence of a vascular surgeon or highly experienced general surgeon, due to the risk of injury to vascular anatomy. Accordingly, there is a need in the art for systems and methods that facilitate access to the spine, thereby simplifying surgical procedures and expediting patient recovery.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for accessing intervertebral space and inserting spine implants between vertebral bodies. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

The present invention provides access to the spine through the use of a postero-lateral approach. A minimally invasive dilation and/or access device employing such an approach would have significant advantages in spinal orthopaedic procedures over the lateral and anterior approaches. These advantages may include avoiding the need to turn the patient during surgery, less muscle retraction, less blood loss, less operating room time, minimized damage to the vascular system, organs, nerves and muscles, faster recovery, and an improved overall outcome for the patient.

Figure 1:
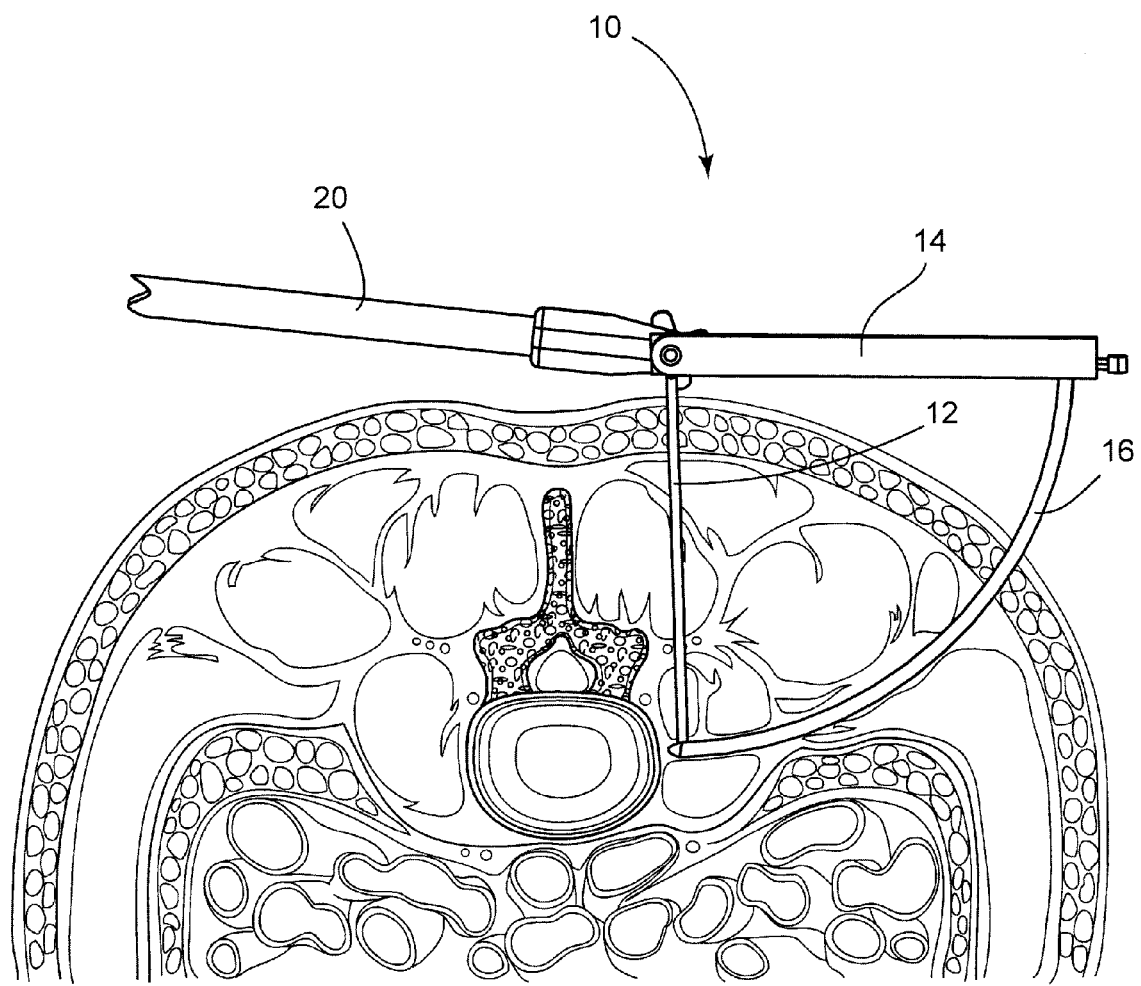
FIG. 1 is a cephalad view of a cross-section of a portion of a patient with an arcuate cannula assembly deployed adjacent a portion of the spine.

Referring to FIG. 1, one embodiment of an arcuate cannula assembly 10 is shown. The assembly 10 comprises a targeting post 12, a guide arm 14, and a curved penetrating guide member 16. An instrument support arm 20 holds the assembly and connects to an operating table (not shown). The assembly 10 may further comprise a series of graduated curved cannulas (shown in FIG. 11), which are introduced sequentially over the guide member 16 to create access to a targeted portion of a spine. Use of the arcuate cannula assembly 10 creates an access portal to the intervertebral disc space or any element of the anterior spinal column through an arcuate path, from a postero-lateral approach. The access portal is an unimpeded passage through which surgical instruments, implants and other materials may be passed to complete a variety of intervertebral procedures. This arcuate postero-lateral approach may be advantageous in performing a number of procedures, including but not limited to: implantation of motion preservation devices, total disk replacement, implantation of interbody devices, discectomy, lateral plating with or without dynamic elements, vertebra fixation or graft compression using plates or staples, foraminotomy, decompression, annulotomy, nucleotomy, annulus or nucleus repair, vertebral body biopsy, vertebroplasty, height restoration of a collapsed vertebral body (vertebral body augmentation), implantation of a fusion cage with stabilization features, implantation of a fusion cage with teeth to hold endplates together, or implantation of a curved or straight staple across the disc space to provide compression on the cage and stabilization of the cage.

Figure 2:
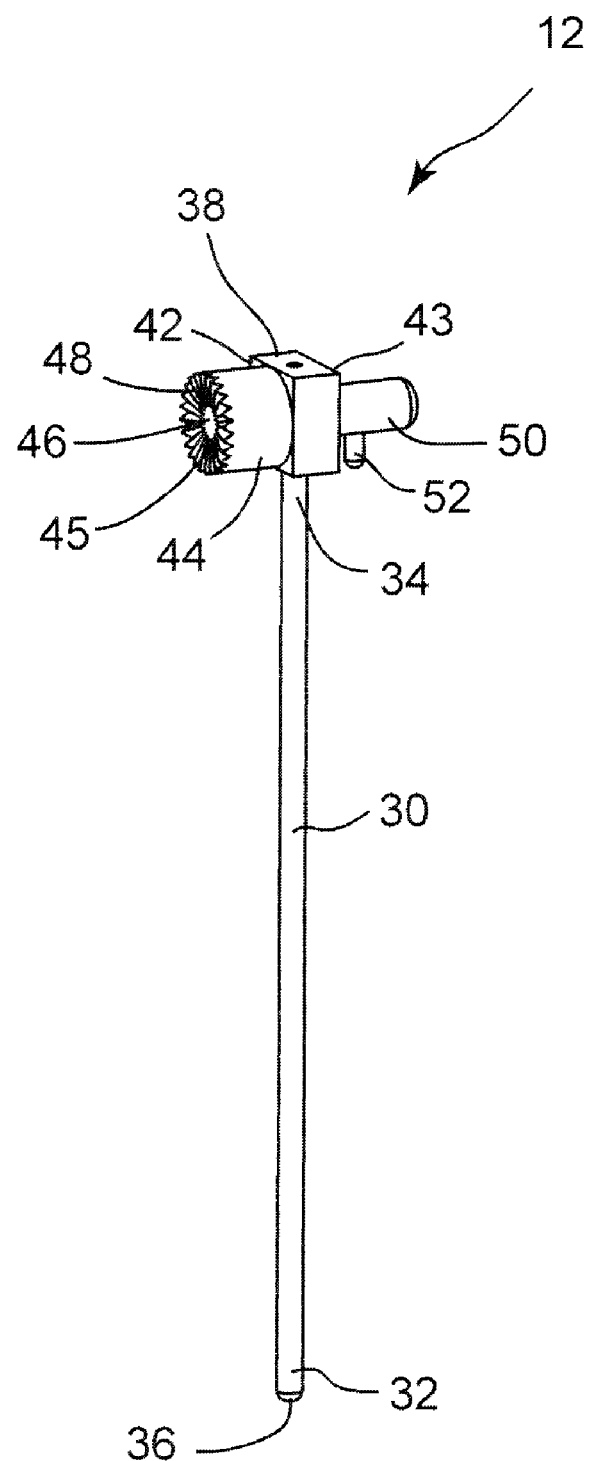
FIG. 2 is a perspective view of a targeting post of the arcuate cannula assembly of FIG. 1.

Referring to FIG. 2, a perspective view of the targeting post 12 is shown. The targeting post 12 comprises an elongate shaft 30 with a distal end 32 and a proximal end 34. A rounded tip 36 is at the terminus of the distal end 32. The proximal end 34 adjoins a rectangular connector block 38 which has a first side 42 and a second side 43. Adjoining the connector block 38 on the first side 42 is a support arm attachment post 44. The attachment post 44 has a receiving slot 46 which extends transversely into the attachment post through an interface surface 45. In the preferred embodiment the receiving slot 46 includes an internally threaded surface. A radial spline 48 encircles the receiving slot 46 on the interface surface 45. Adjoining the connector block 38 on the second side 43 is a rotation post 50. Extending distally from the rotation post 50 is an optional stop feature 52.

Figure 3:
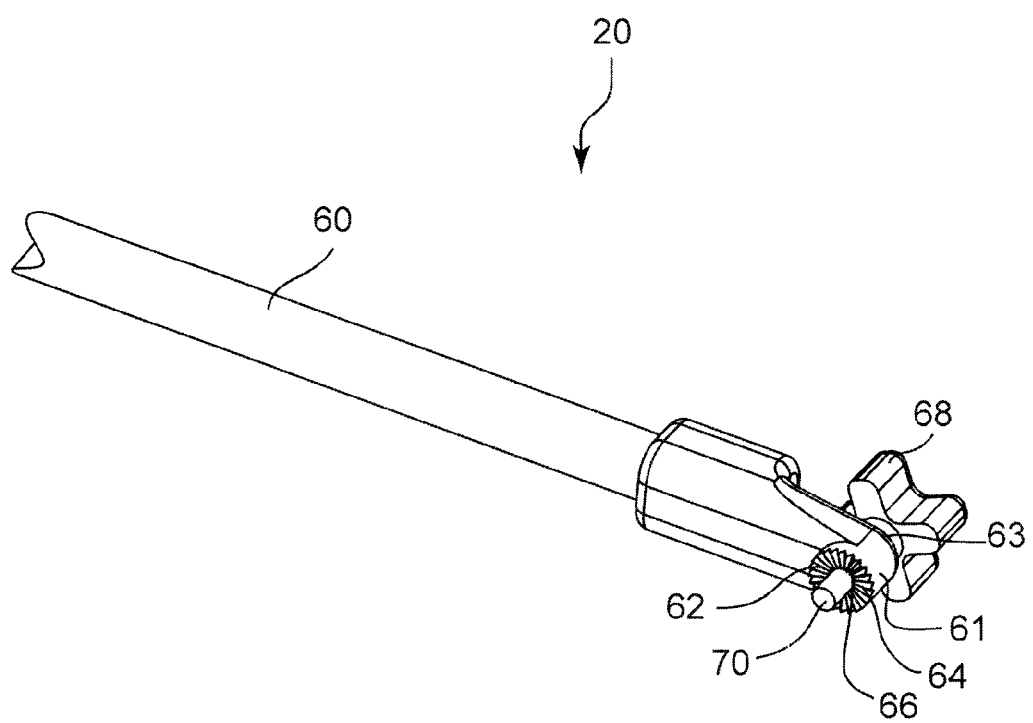
FIG. 3 is a perspective view of a portion of an instrument support arm.

Referring to FIG. 3, a perspective view of a support arm 20 is shown. The support arm 20 comprises a shaft 60 which attaches to the operating table via various linkages, pivots, or connections to allow multiple degrees of freedom to accommodate the positioning of the instrument to be held. A wide variety of differently-configured instrument support arms are well known in the art and the assembly 10 may be compatible with the instrument support arm of choice for the surgeon.

A distal end 61 of the shaft 60 has a first side 62 and a second side 63. Extending transversely through the distal end 61 from the first side 62 to the second side 63 is a screw channel 66. On the first side 62, an interface surface 65 has a radial spline 64 which encircles the opening of the screw channel 66. The radial spline 64 is configured to mate with the radial spline 48 on the targeting post 12 when the post is connected to the support arm 20. Extending through the channel 66 is a thumb screw 68, and a shaft 70 protrudes from the channel 66 on the second side 63. In the preferred embodiment, shaft 70 includes an externally threaded surface configured to interface with the threaded receiving slot 46 on the targeting post 12.

Figure 4:
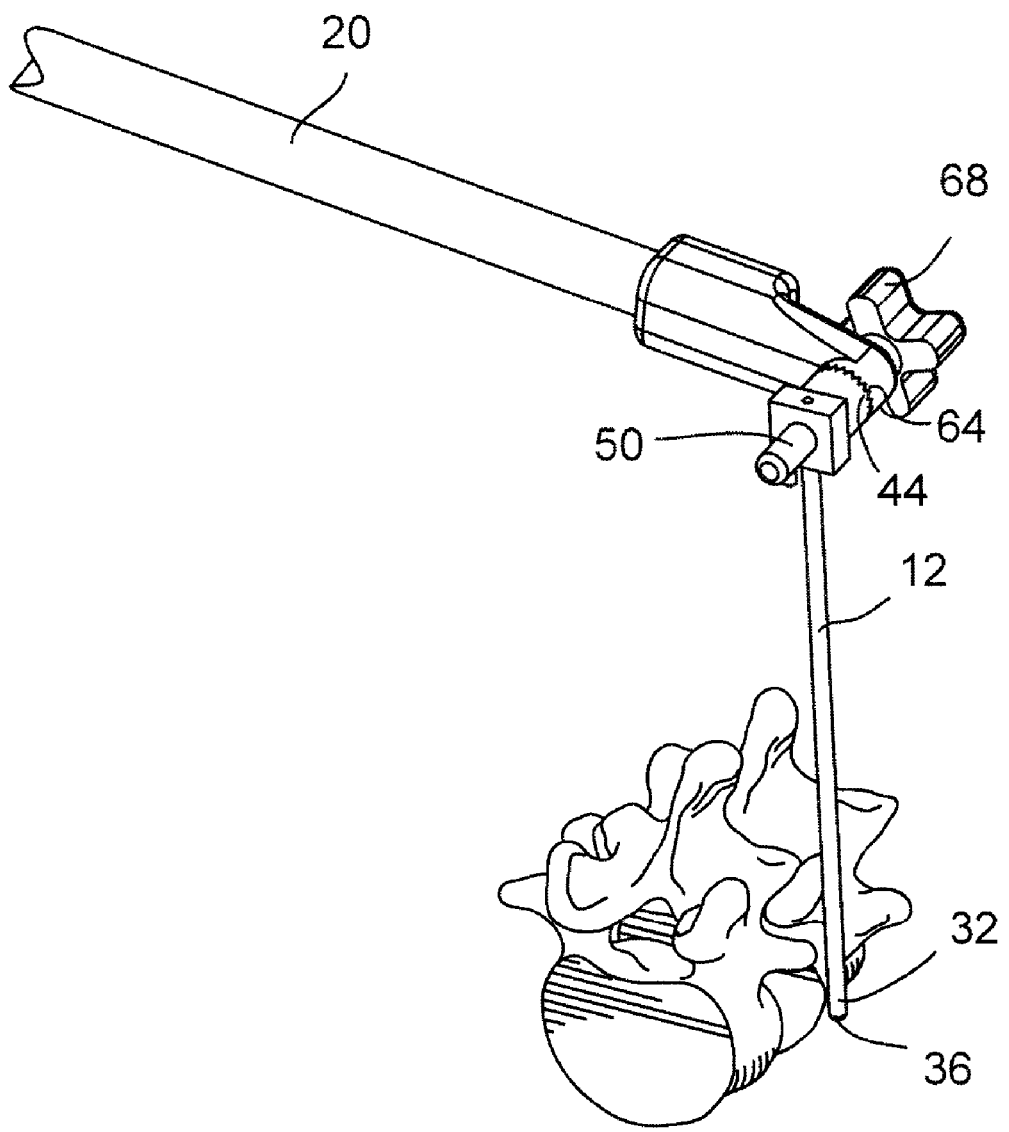
FIG. 4 is a perspective view of the instrument support arm of FIG. 3 supporting the targeting post of FIG. 2 adjacent a portion of a spine.

Referring to FIG. 4, the targeting post 12 is introduced into the patient from a postero-lateral approach through a small incision on the patient's back posterior to the targeted spine segment. The distal end 32 of the targeting post 12 is advanced antero-medially through the patient just lateral to the targeted intervertebral disc until the tip 36 reaches a desired reference location at the anterior lateral half or one third of the disc. The blunt shape of the tip 36 gently pushes tissues aside as the post 12 is advanced in. The post 12 may also be wired as an electrode during insertion, allowing for nerve monitoring or electromyography (EMG) to avoid nerves as the post 12 advances through the tissues. Of special concern is avoidance of the nerve roots exiting the spinal column as the psoas muscle adjacent to the spine is penetrated by the post 12. The targeting post 12 is inserted so that it is coplanar with the superior endplate of the inferior vertebral body for the intervertebral level to be treated. Preferably, the post 12 is aligned parallel with the sagittal plane of the patient, but other orientations are possible if necessary to avoid nerves or other obstacles.

When the distal end 32 of the targeting post 12 has reached the reference location, the proximal end 30 is attached to the support arm 20 via the thumb screw 68. The protruding screw shaft 70 is threaded into the receiving slot 46. As the thumb screw 68 is threaded in, the radial splines 44, 64 mesh, locking the targeting post 12 to the support arm 20. Once attachment is made between the targeting post 12 and the support arm 20, the various degrees of freedom of the support arm 20 are locked down to provide sufficiently rigid instrument stabilization. In position adjacent to the spine, the targeting post 12 acts as a stabilizing and reference guide for subsequent cannulas, instruments and implants.

Figure 5:
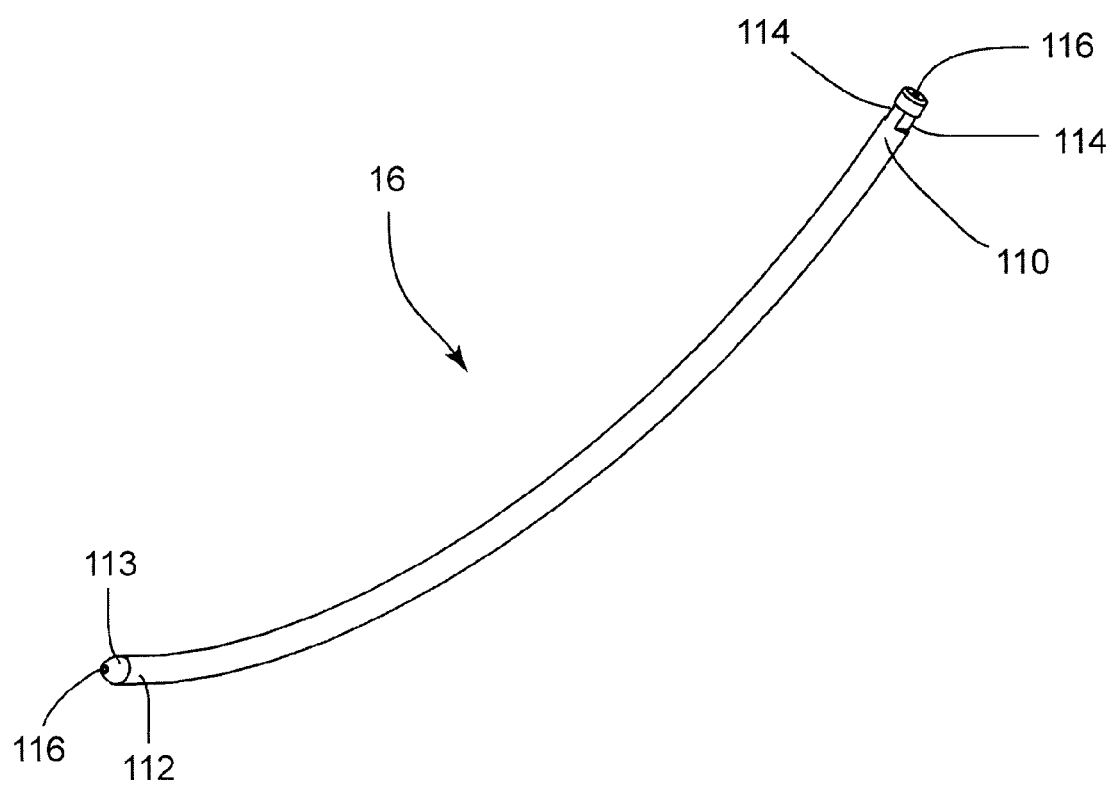
FIG. 5 is a perspective view of a guide member of the arcuate cannula assembly of FIG. 1.

Referring to FIG. 5, the penetrating guide member 16 is shown. The guide member 16 is curved and may be arcuate (i.e., may extend along a fixed radius of curvature). The guide member 16 has a proximal end 110, and a distal end 112 with an insertion tip 113. The insertion tip 113 may be rounded or optionally pointed, to penetrate muscles and fascia. Two attachment recesses 114 at the proximal end facilitate attaching the guide member 16 to the guide arm 14, and are also configured to connect to an instrument support arm. A narrow channel may optionally extend the length of the guide member 16, sized to receive a wire for nerve monitoring or EMG during dilation.

Figure 6A:
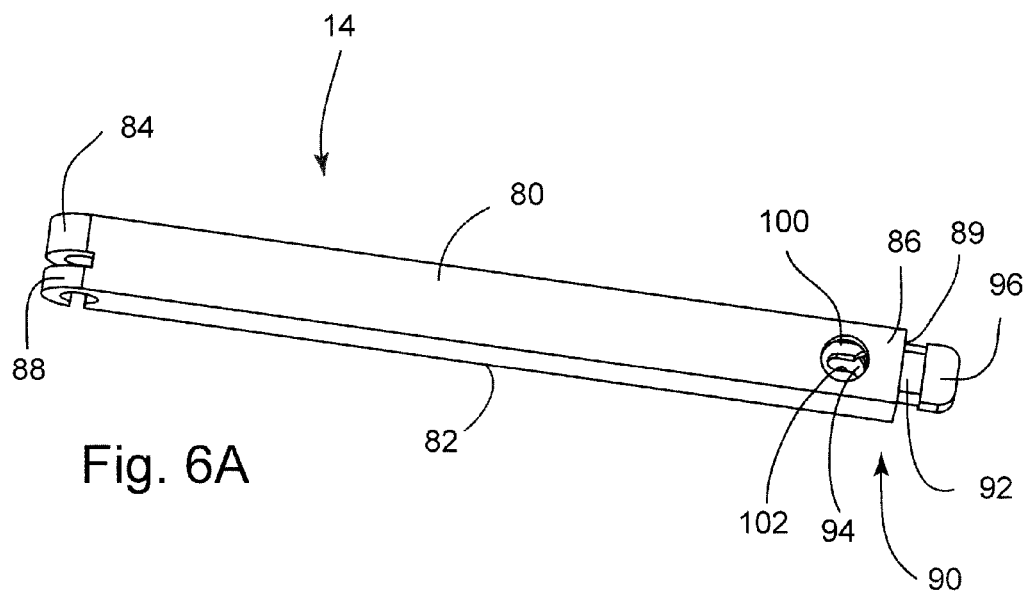
FIG. 6A is a perspective view of a guide arm of the arcuate cannula assembly of FIG. 1.

Referring to FIG. 6A, a perspective view of the guide arm 14 is shown. The guide arm 14 has a first side 80 and a second side 82. At a proximal end is a pinned end 84; a latch end 86 is at the opposite distal end. The pinned end 84 has an attachment feature 88 which is shaped to rotatably attach to the rotation post 50 on the targeting post 12. Inserted into a horizontal slot 89 in the latch end 86 is a spring loaded guide member latch assembly 90 which is shaped to grip the penetrating guide member 16. The guide member latch assembly 90 has a sliding latch bar 92 with a keyhole 94 and a tab 96. On the first side 80 of the guide arm 14, near the latch end 86 is a round guide member opening 100. Directly opposite it on the second side 82 may optionally be a smaller pinhole opening 102.

Figure 6B:
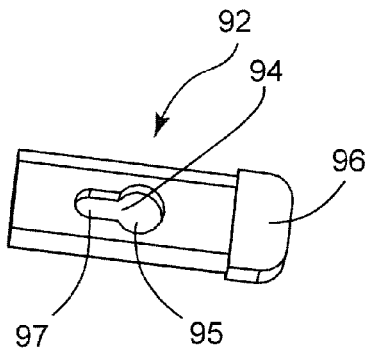
FIG. 6B is a perspective view of a sliding latch bar of the guide arm of FIG. 6A.

FIG. 6B is an enlarged view of the sliding latch bar 92. Keyhole 94 has a rounded lobe 95 disposed toward the tab 96, and an ovoid lobe 97 opposite the tab 96. The rounded lobe 95 is sized to fit around the proximal end 110 of the guide member 16. The ovoid lobe 97 is sized to hold the attachment recesses 114 of the guide member 16. The tab 96 may be grasped to move the sliding latch bar 92 within the horizontal slot 89. A spring (not shown) is disposed in the horizontal slot 89 to provide resistance against the sliding latch bar 92.

Figure 7:
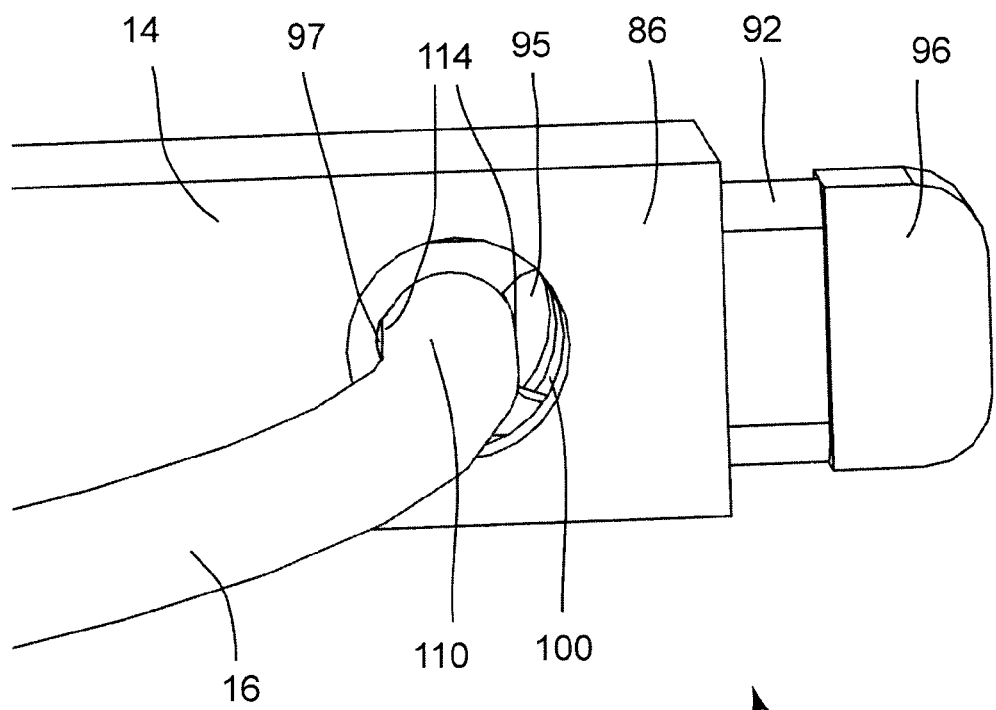
FIG. 7 is a perspective view of a latch assembly of FIG. 6A, with the guide member of FIG. 5 latched thereto.

FIG. 7 is an enlarged view of the latch end 86 of the guide arm 14, showing the guide member 16 latched in the latch assembly 90. To latch the guide member 16 in the latch assembly 90, first the sliding latch bar 92 is introduced into the horizontal slot 89 until the rounded lobe 95 of the keyhole 94 lines up with the guide member opening 100. The proximal end 110 of the guide member 16 is inserted such that the attachment recesses 114 are adjacent to the lined up keyhole 94 and opening 100. The sliding latch bar 92 is released, and the spring (not shown) pushes the sliding latch bar 92 distally until the ovoid lobe 97 of the keyhole 94 slides around the attachment recesses 114 of the guide member 16. The force of the spring traps the guide member 16 in the latch assembly 90, as the guide member is pinned between the ovoid lobe 97 and the latch end 86 of the guide bar 14 adjacent the guide member opening 100.

Figure 8:
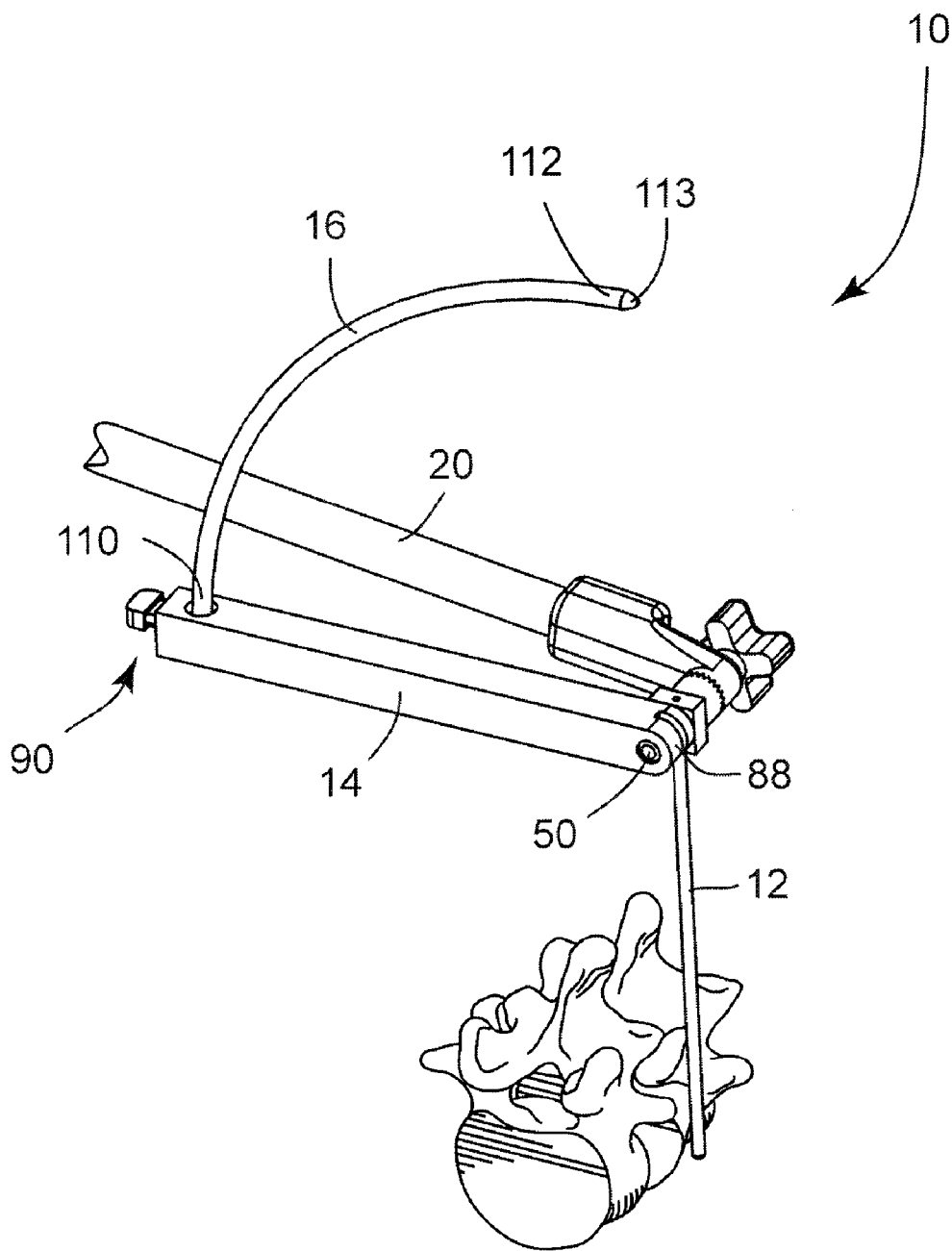
FIG. 8 is a perspective view of the arcuate cannula assembly of FIG. 1 with the guide arm in a first position, adjacent a portion of the spine.

Referring to FIG. 8, the support arm 20, targeting post 12, guide arm 14 and penetrating guide member 16 are shown, with the guide arm 14 and penetrating guide member 16 in a first position. The attachment feature 88 on the guide arm 14 is engaged with the rotation post 50 on the targeting post 12. Thus attached, the guide arm 14 can rotate about the axis of the rotation post 50; however the stop feature 52 on the rotation post 50 may prevent the guide arm 14 from rotating entirely about the rotation post 50. The guide arm 14 is sized to match the radius of the curve of the penetrating guide member 16, such that the arc centerpoint of the penetrating guide member 16 is coincident with the center of rotation, or axis of the rotation post 50. The guide member latch 90 holds the penetrating guide member 16 as seen in FIG. 7.

Figure 9:
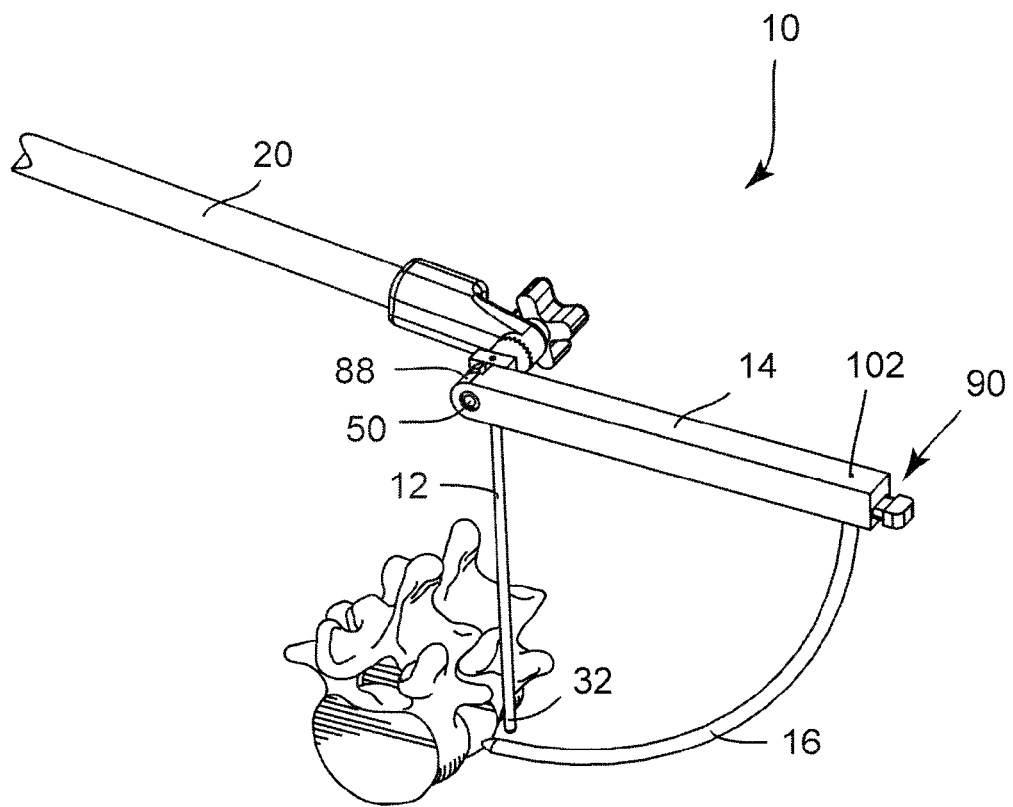
FIG. 9 is a perspective view of the arcuate cannula assembly of FIG. 1 with the guide arm in a second position, adjacent a portion of the spine.

After the penetrating guide member 16 is attached to the guide arm 14, the guide arm 14 is rotated so that the insertion tip 113 of the guide member 16 makes contact with the skin. At this point, the guide member 16 is lifted and an incision of approximately 1-5 cm is made into the skin and fascia. As shown in FIG. 9, the guide member 16 is then advanced into the incision via rotation of the guide arm 14. The guide member penetrates the soft tissues and fascia of the patient, and is advanced antero-medially along an arcuate path until the insertion tip 113 is at the lateral margin of the targeted disc, at a target location. The target location is at a known position relative to the reference location provided by the distal end 32 of the targeting post 12, as the guide bar 14 holds the guide member 16 in a fixed relationship as the guide bar 14 rotates about the rotation post 50. At this point the guide arm and guide member are in a second position. The guide member 16 may have a rounded insertion tip, or a sharp, pointed insertion tip if necessary to penetrate the tissues. EMG monitoring may be used to ensure safe passage of the guide member through the fascia. The optional pinhole opening 102 creates access for a wire to pass through the guide arm into the guide member 16 if it is desirable to connect an electrode to the guide member 16 for nerve monitoring. The stop feature 52 (seen in FIG. 2) stops rotation of the guide arm 14 and prevents the guide member 16 from extending past the margin of the disc and contacting the spinal cord.

Once the guide member 16 is correctly positioned adjacent the targeted location, the guide arm 14 is detached from the guide member 16 and the targeting post 12. The guide member 16 is left in the patient to serve as a guide for one cannula or series of cannulas which are graduated in size, and which are inserted sequentially from smaller to larger to increase the cross-sectional area of the access portal to the area to be treated.

Figure 10:
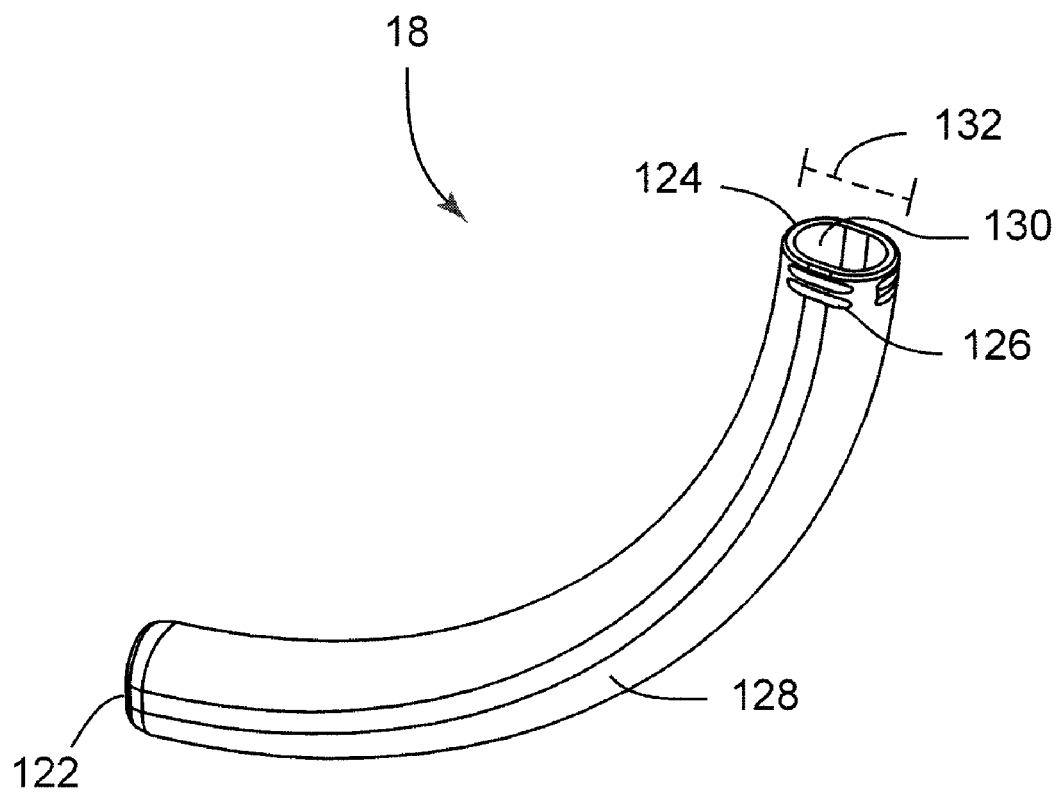
FIG. 10 is a perspective view of a cannula.

Referring to FIG. 10, a single cannula 18 is shown. The cannula 18 is curved and generally tubular in form, with a tubular support wall 128 which has an open distal end 122 and an open proximal end 124. The distal end 122 is rounded so that tissues are pushed aside gently as the cannula is inserted through the patient. A bore 130 runs the length of the cannula 18 from the open distal end 122 to the open proximal end 123, and provides access to the targeted spinal area for instrument insertion, and insertion and removal of interbody devices, arthroscopic devices, implants, bone graft materials, bone cement, and other materials and devices. A cross-sectional shape of the support wall 128 of the bore 130 is generally curved, and may specifically be round, oval, elliptical or another curved shape. The open proximal end 123 has a plurality of grip features 126 which allow the surgeon to grip the cannula. Optionally, the cannula 18 may have attachment features to allow attachment of the cannula to the instrument support arm. The cannula 18 may optionally be substantially radiolucent, and can comprise biocompatible polymers, elastomers, ceramics, or aluminum or other metals. The curve of the cannula 18 may be arcuate, and may sweep through an angle of about 90° such that the open proximal and distal ends 124, 122 are substantially perpendicular to each other.

Figure 11:
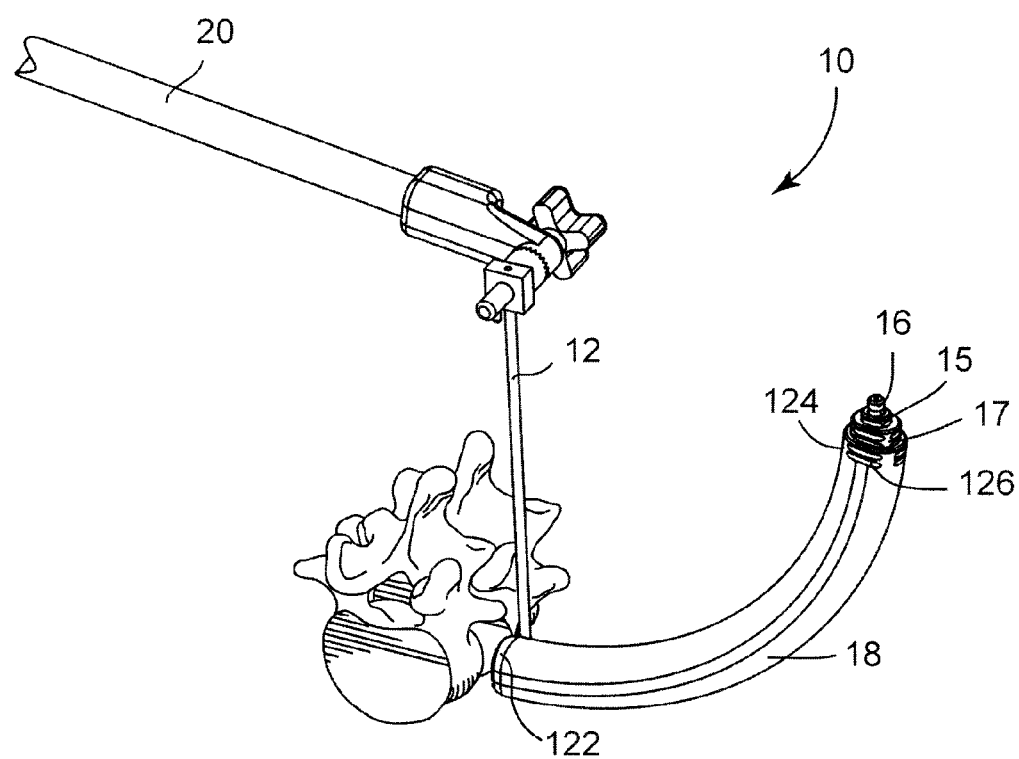
FIG. 11 is a perspective view of the arcuate cannula assembly of FIG. 1 with the guide arm removed and several cannulas added, adjacent a portion of the spine.

Referring to FIG. 11, a series of graduated cannulas 15, 17, 18 are inserted one at a time over the proximal end 110 of the penetrating guide member 16, and advanced antero-medially over the guide member 16 until the corresponding distal end reaches the distal end 112 of the guide member 16. Each cannula 17, 18 is shorter in length and larger in cross-sectional area than the next smallest cannula, to allow the surgeon to grip each cannula as it is installed and removed. As each cannula 15, 17, 18 is inserted, the access portal through the soft tissues and fascia is increased in size, creating increased access to the targeted portion of the spine. The number of cannulas inserted is determined by the desired cross-sectional area of the opening to the spine; in many instances two to five cannulas will be inserted. Once all cannulas 15, 17, 18 are inserted around the penetrating guide member 16, the guide member 16 and the inner cannulas 15, 17 are removed, leaving the largest cannula 18 in the patient. This cannula may be attached via an attachment feature (not shown) to the support arm 20, to provide additional stabilization for removal of the smaller cannulas, and for subsequent instrument insertion and procedures.

In one embodiment of the invention, the largest cannula 18 may have a tooth portion (not shown) which extends longitudinally from the insertion end 122. During insertion, the tooth portion is placed between the superior and inferior endplates of the intervertebral space, to assist in maintaining access to the space.

Figure 12:
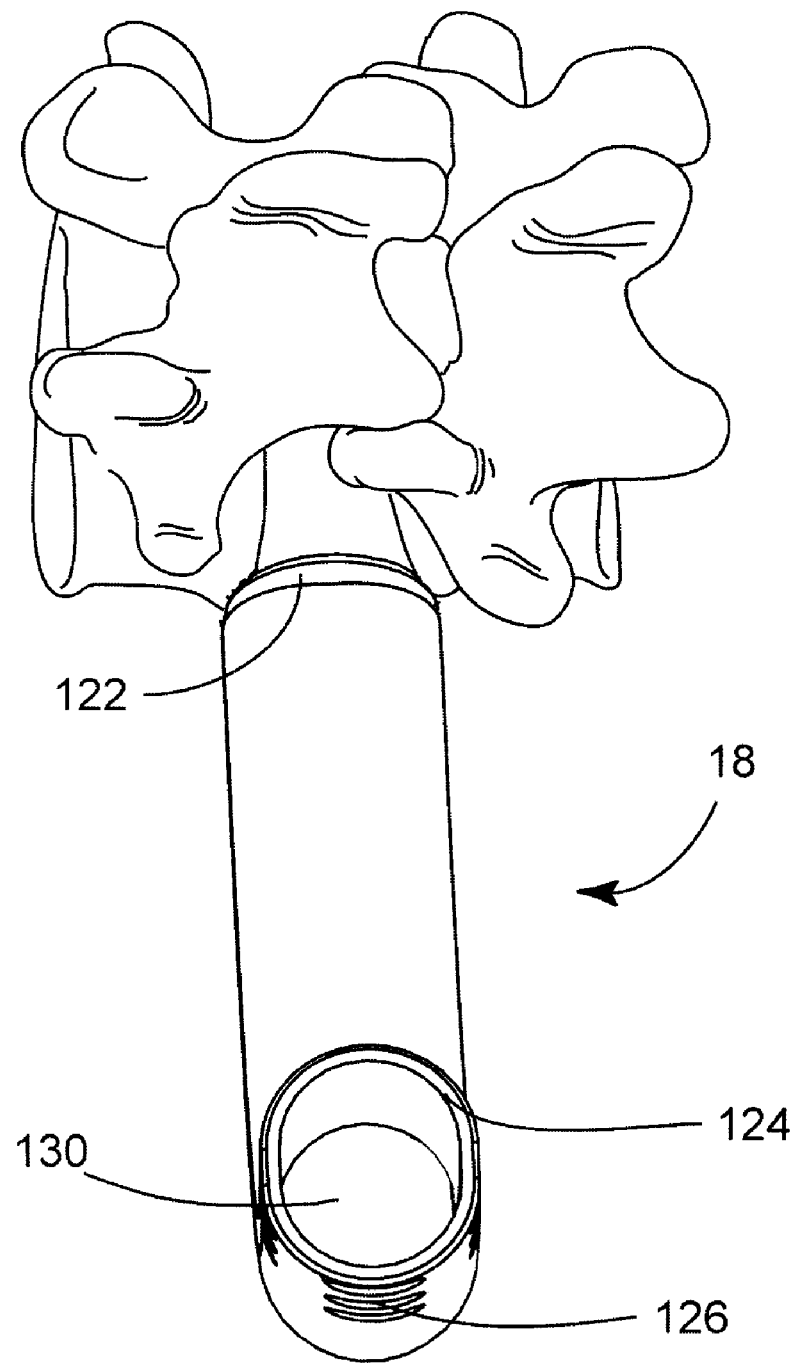
FIG. 12 is a postero-lateral perspective view of a cannula of FIG. 10 adjacent a portion of the spine.

FIG. 12 is a postero-lateral view of a portion of a spine with a cannula inserted according to the procedure previously described. When in place in the patient, the bore 130 of the cannula 18 is an access portal through which surgical instruments, implants and other materials may be passed to complete a variety of intervertebral procedures. Surgical instruments used in conjunction with the cannula 18 may have rigid, curved shafts or flexible shafts to navigate through the cannula 18 to the intervertebral space. The cannula 18 may be sized to accommodate passage of an interbody fusion implant 300 (shown in FIGS. 15A and 15B).

Figure 13:
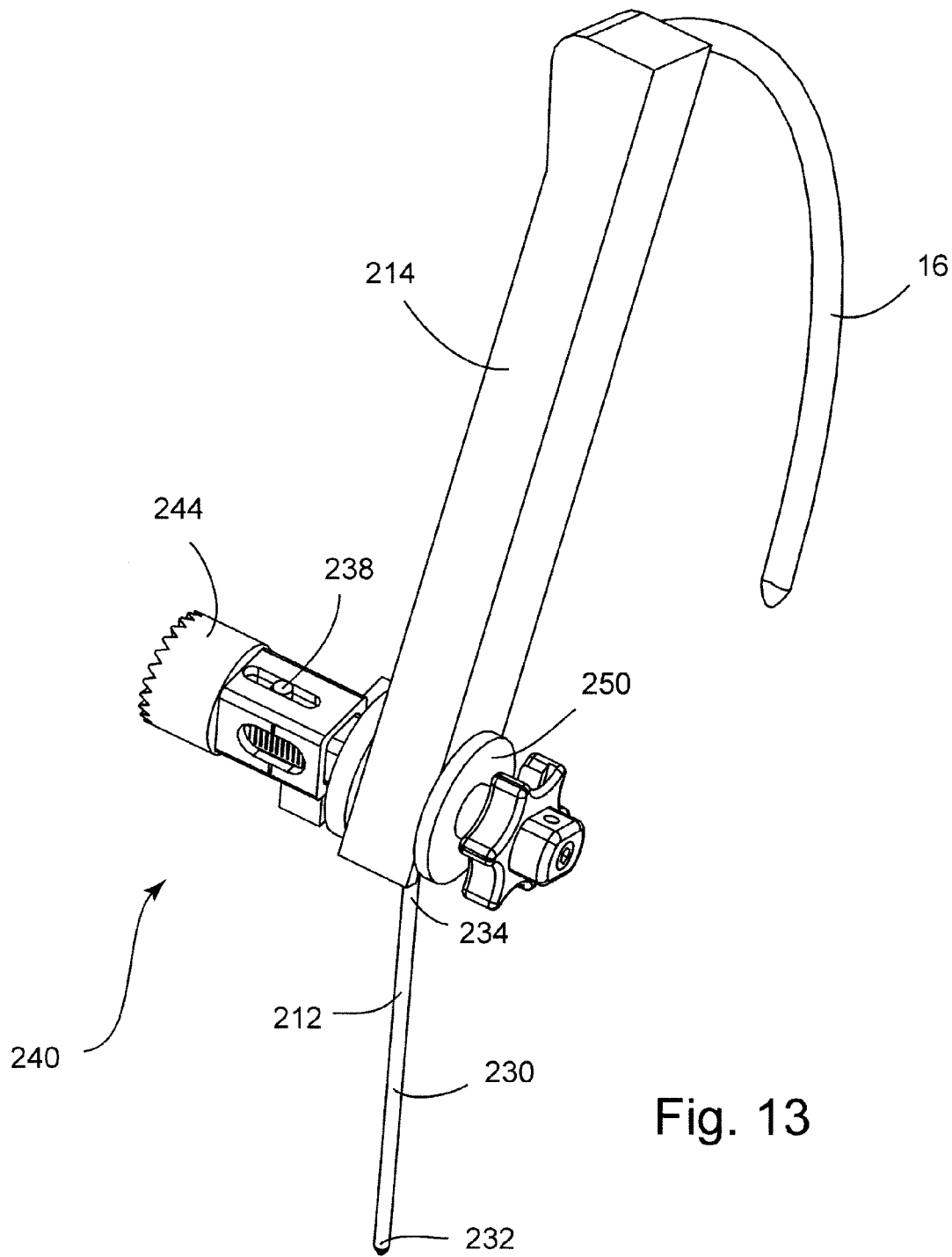
FIG. 13 is a perspective view of an arcuate cannula assembly with an adjustable targeting post.

Another embodiment of the invention comprises a targeting post which is capable of cephalad-caudal adjustment. FIG. 13 is a perspective view of an arcuate cannula assembly 210 which includes an adjustable targeting post 212, a guide arm 214 and a penetrating guide member 16. The adjustable targeting post 212 has a shaft 230 which has a distal end 232 and a proximal end 234. Proximally adjacent to the proximal end 234 of the shaft 230 is a connection portion 240, which extends in a cephalad-caudal direction and comprises a guide arm connector 250, a cephalad-caudal adjustment feature 238, and a support arm attachment post 244. The cephalad-caudal adjustment feature 238 can be adjusted to lengthen or shorten the cephalad-caudal length of the connection portion 240. Thus, after the targeting post is inserted into the patient, the length of the connection portion 240 can be adjusted as necessary to attain the necessary offset to adjust the resultant cephalad-caudal distance between the guide member 16 and the targeting post 212. The adjustment allows the target location to vary along the cephalad-caudal direction such that the known position of the target location is offset relative to the reference location. Cephalad-caudal offset of the guide arm 214 and the attached guide member 16 may be useful in avoidance of nerve structures and other objects during the dilation process.

Figure 14:
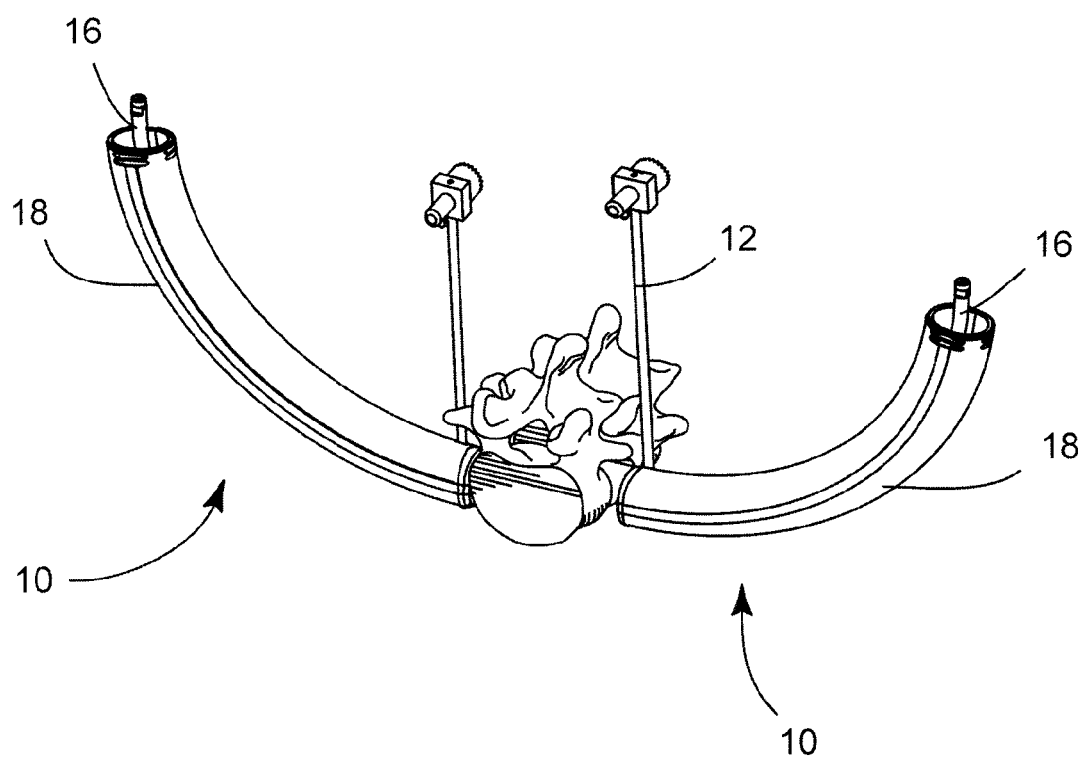
FIG. 14 is a perspective view of two arcuate cannula assemblies of FIG. 1, adjacent two lateral sides of a portion of the spine.

Another application of the invention comprises a bilateral implementation of two arcuate cannula assemblies. In this embodiment, two assemblies 10 are used together, one on each lateral side of the spine. Referring to FIG. 14, portions of two assemblies 10, which comprise two targeting posts 12, two penetrating guide members 16, and two cannulas 18, are shown adjacent to each lateral side of the spine. This embodiment permits enhanced access to the targeted area, since access may be attained from both lateral sides simultaneously. Instruments, implants, or other materials may be pushed or pulled into the intervertebral space, or through the entire access pathway.

Figure 15A:
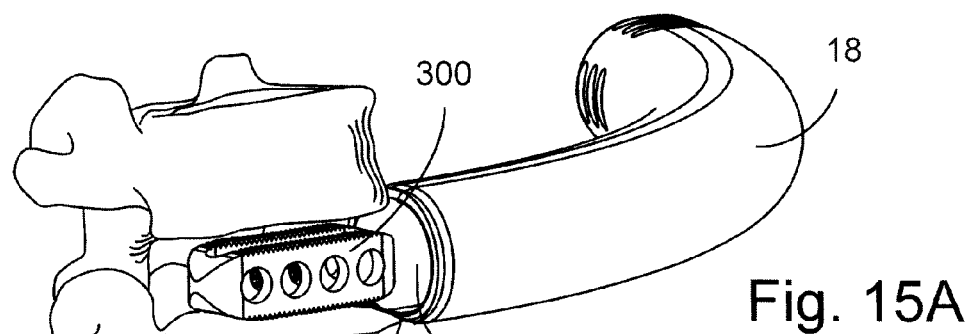
FIG. 15A is an antero-lateral perspective view of the cannula of FIG. 10 adjacent a portion of a spine, and an interbody device in an intervertebral space.
Figure 15B:
FIG. 15B is a perspective view of the interbody device of FIG. 15A.
Figure 15B:
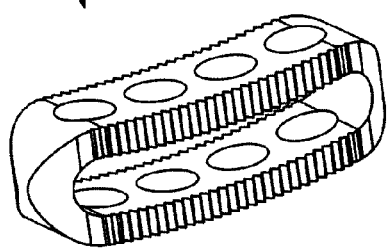

Another embodiment of the invention further comprises an interbody device. FIG. 15A is an anterior perspective view of a portion of a spine with a cannula 18 and an interbody device 300 which may be inserted through the arcuate cannula assembly previously disclosed. FIG. 15B is a perspective view of the interbody device 300 of FIG. 15A. The interbody device 300 has a generally rectangular box-like shape, and is slightly curved along its longitudinal axis. The interbody device 300 may optionally have a radius of curvature substantially the same as that of the cannula 18.

In any case, the bore 130 of the cannula 18 is sized to accommodate passage of the interbody device 300. Because use of the arcuate cannula assembly 10 allows improved access to the intervertebral space, the interbody device 300 may have a larger footprint than many other interbody devices, and can extend across most of the medial-lateral width of the intervertebral space, to provide for increased stability, increased bone in-growth, and improved fusion. A curved insertion tool and curved tamp (not shown) are used to insert and seat the interbody device 300 in the intervertebral space. In the alternative, a flexible insertion tool and/or a flexible tamp may be used.

The arcuate postero-lateral approach described above may have many advantages for spinal procedures, particularly procedures involving anterior vertebral column elements. This approach may be used to insert motion preservation devices, such as total disc replacements. By accessing the disc space via an arcuate postero-lateral approach, the surgeon is able to spare the anterior longitudinal ligament as well as avoid complications with the great vessels. This approach also provides for revision options with virtually the same instrumentation and implant designs by accessing the disc space from the opposite lateral side as the first surgery. This approach also allows for total disc replacement (TDR) endplate retention features which are more desirable than anterior approach TDR features, such as endplate keels or teeth which are oriented in the frontal plane to resist the high shear loads seen in the lumber spine lordotic region.

This approach may also be used for various intervertebral disc treatment or resection procedures such as annulotomy, nucleotomy, discectomy, annulus replacement, nucleus replacement, and decompression due to a bulging or extruded disc. During an annulotomy, the surgeon may provide an access portal in the manner described previously, and open and/or remove a portion or all of the disc annulus. During a nucleotomy, the surgeon may provide an access portal in the manner described previously, and open and/or resect a portion of the intervertebral disc nucleus. During a discectomy, the surgeon may remove a portion or the entire intervertebral disc through the access portal in order to accomplish decompression of the nerve roots, dura, or spinal cord. This procedure may be done as a conservative therapy to relieve patient symptoms or pain, or it may be done in preparation for total disc replacement or fusion.

For annulus repair or replacement, the arcuate postero-lateral approach may facilitate a larger needle and avoidance of complicated vascular structure and may allow a pathway for a prosthetic annulus to be placed or formed in the intervertebral space. Using a bilateral arcuate approach such as that depicted in FIG. 14 could further facilitate the creation of bounding elements, such as a shield, guard, mold, or equivalent such that the annulus may be repaired, formed, inserted, created, or augmented. Similar benefits are realized for a nucleus replacement procedure where all or a portion of the intervertebral nucleus is repaired or resected and replaced, created or augmented via various techniques. A prosthetic nucleus may be delivered via a passageway that is larger than that afforded by a transpedicular approach, and less complicated and less risky than an anterior approach, by using the arcuate postero-lateral approach described above. Various intervertebral disc treatment methods have been postulated, such as using electrosurgical therapies. It is readily apparent to one of skill in the art how conducting these therapies via an arcuate postero-lateral approach may benefit the surgeon as well as improve clinical outcomes.

The arcuate postero-lateral approach may also be utilized for additional vertebral body motion segment stabilization procedures such as interbody device insertion, lateral plating, anterior plating, lateral or anterior plating with dynamic stabilization or compression elements, deformity correction, and/or graft compression devices or procedures. The arcuate postero-lateral access portal such as that depicted in FIG. 15A may facilitate interbody fusion procedures by allowing a single surgical exposure or patient positioning to insert all required stabilization elements such as an interbody fusion device similar to that depicted in FIG. 15B, or posterior stabilization hardware such as pedicle screws, rods, hooks, and facet screws, among others. By approaching the intervertebral disc space with a tangential or almost straight medial-lateral trajectory right next to the vertebral body, the interbody device may more fully occupy the intervertebral space. This may result in a multitude of advantages such a leveraging the higher strength cortical regions on the vertebral body endplates, allowing more cross-sectional surface area or a larger footprint for improved stability, allowing more bone graft surface are to encourage better osteointegration, bony fusion, and 360° fusion. The interbody device may also comprise a lordotic angle which does not require over-distraction such as is the case with transforaminal lumbar interbody fusion (TLIF) and posterior lumbar interbody fusion (PLIF) procedures.

The arcuate postero-lateral approach may also be used for lateral plating procedures, in which the implanted plates may comprise fixed, dynamic, or compressive elements. This approach again allows a single patient positioning to conduct lateral plating as well as posterior stabilization hardware such as screws, hooks and rods. These plates may be used for local deformity correction or prevention procedures to treat local scoliosis, kyphosis, hyper-lordosis, or spondylolisthesis. Additionally, the arcuate postero-lateral approach may allow for novel graft compression devices or procedures that enable the surgeon to apply improved local compressive forces between vertebral bodies or an interbody device. Benefits of improved local compressive forces include improved bone graft incorporation, fusion, interbody device stability, as well as a potentially reduced risk of interbody device expulsion that is often the result of over-compressing the disc space and applying unintended moments via traditional pedicle screws and rods. Such graft compression devices include lateral plates with compression features, vertebral body staples which cooperate with the superior and inferior vertebral bodies to apply compression, and integrated interbody device with arms that cooperate with the vertebral bodies to apply compression via screws, tapered surfaces, or the like.

Various central canal or foraminal decompression procedures may be performed with the arcuate postero-lateral approach described previously. Decompression procedures are conducted to resect soft or hard tissues that may be impinging on neural elements such as the exiting nerve roots, dura, or spinal cord, resulting in various pathologies such as radiolopathy, myelopathy, pain, tingling, numbness, and loss of motor or sensory control. For example, anterior central canal decompression required due to a diseased intervertebral disc is often a difficult procedure. By using the disclosed arcuate postero-lateral approach, this decompression procedure allows for improved patient positioning, access, and patient outcomes. Foraminal decompression procedures via an arcuate postero-lateral approach may also allow the surgeon an improved trajectory and passageway to decompress the foramen.

Procedures involving the vertebral body, such as vertebral body biopsy, vertebral body height restoration, and vertebroplasty may successfully utilize the arcuate postero-lateral approach. Often patients who are experiencing symptoms associated with vertebral body disease, collapse, or fracture will undergo a biopsy of the vertebral body to assess the condition of the structure. Osteoporotic patients, especially female geriatric patients, may experience vertebral body collapse or fracture. This is an extremely painful and debilitating condition which may be addressed via vertebroplasty through the disclosed arcuate postero-lateral approach. Often, vertebroplasty, kyphoplasty or arcuplasty procedures are conducted via a transpedicular approach, to inject a hardenable compound such as PMMA cement into the vertebral body to create an internal cast-like structure to stabilize the bony fragments or fractures. The arcuate postero-lateral approach has numerous advantages for such a procedure. It may allow for a larger access needle than a transpedicular approach and accordingly reduces pressure requirements for the viscous hardenable compounds. In addition, it will likely result in less post-operative pain due to not violating the pedicle, and it allows for a more preferable trajectory of the access needle. Vertebroplasties conducted via a transpedicular approach often require a bilateral approach for sufficient vertebral body stabilization. By using the trajectory of the arcuate postero-lateral approach, the surgeon or radiologist may use a single needle and single approach for a complete fill, because the access needle can be advanced to the distal portions and gradually retracted during injection to accomplish a complete fill.

Vertebral body height restoration procedures have recently been disclosed in the art to address collapsed vertebral bodies. The arcuate postero-lateral approach may facilitate such vertebral height restoration procedures by removing the size limitation imposed by the transpedicular approach. Additionally, the ability to access the lateral margins of the vertebral body may be beneficial in insertion of an implant to restore vertebral height and fix it in place via a hardenable compound, or conduct an internal vertebral body distraction and secure the vertebral body via a hardenable compound.

The present invention may be embodied in other specific forms without departing from its spirit or essential characteristics. For example, above are described various alternative examples of systems for accessing intervertebral space. It is appreciated that various features of the above-described examples can be mixed and matched to form a variety of other alternatives. It is also appreciated that this system should not be limited creating access to the intervertebral space. This arcuate access system may be used to obtain access to any portion of the spine. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for creating an access portal to a spine, comprising: positioning a curved guide member to extend along an arcuate path having a fixed radius from an opening in the skin to a target location proximate the spine;
   connecting a guide bar to a proximal end of a curve guide bar to a proximal end of the curved guide member such that a distal end of the curved guide member is constrained to move along the curved path
   inserting a distal end of a bore of a first curved cannula over a proximal end of the curved guide member;
   moving a the bore of a the first curved cannula over the curved guide member along the curved path from the proximal end of the curved guide member toward a distal end of the curved guide member; and
   withdrawing the curved guide member from the bore to provide the access portal through the bore along the curved path.

2. The method of claim 1, wherein positioning the curved guide member along the curved path further comprises moving the curved guide member along the curved path in an antero-medial direction from the opening in the skin to the target location.

3. The method of claim 1, wherein positioning the curved guide member further comprises rotating the guide bar relative to a fixed point to guide the distal end of the curved guide member along the arcuate path.

4. The method of claim 1, further comprising securing a support arm to the first curved cannula to provide movable or fixed support to the first curved cannula.

5. The method of claim 1, further comprising inserting an interbody fusion implant through the bore along the curved path to a position between two vertebrae.

6. A method for creating an access portal to a spine, comprising:
   percutaneously positioning a distal end of a targeting post at a reference location proximate a portion of the spine;
   coupling a curved guide member to the targeting post such that motion of the curved guide member is confined to a curved path terminating at a target location having a known position relative to the reference location;
   moving the curved guide member along the curved path;
   uncoupling the curved guide member from the targeting post;
   inserting a distal end of a first curved cannula over a proximal end of the curved guide member; and
   sliding the first curved cannula along the curved path from the proximal end of the curved guide member toward a distal end of the curved guide member to provide access to the spine proximate the target location.

7. The method of claim 6, wherein sliding the first curved cannula along the curved path comprises sliding the first curved cannula along the curved path in an antero-medial direction from an opening in the skin to the target location.

8. The method of claim 6, wherein moving the curved guide member along the curved path comprises moving the curved guide member along an arcuate path having a fixed radius, and wherein sliding the first curved cannula along the curved path comprises sliding the first curved cannula along the arcuate path.

9. The method of claim 8, wherein moving the curved guide member along the arcuate path further comprises latching a guide bar to a proximal end of the curved guide member such that a distal end of the curved guide member is constrained to move along the arcuate path.

10. The method of claim 9, wherein coupling the curved guide member to the targeting post further comprises linking the guide bar to a proximal end of the targeting post such that the guide bar rotates relative to the proximal end of the targeting post to guide the distal end of the curved guide member along the arcuate path.

11. The method of claim 6, further comprising adjusting an adjustment feature of the targeting post to vary the target location in a cephalad-caudal direction relative to the reference location.

12. The method of claim 6, further comprising securing a support arm to the first curved cannula to provide movable or fixed support to the first curved cannula.

13. The method of claim 6, further comprising inserting an interbody fusion implant through the bore along the curved path to a position between two vertebrae.

14. The method of claim 6, further comprising withdrawing the curved guide member through a proximal end the first curved cannula.

15. A method for creating an access portal to a spine, comprising:
percutaneously positioning a distal end of a targeting post at a reference location proximate a portion of the spine;
coupling a curved guide member to the targeting post such that motion of the curved guide member is confined to a curved path terminating at a target location having a known position relative to the reference location;
moving the curved guide member along the curved path;
sliding the first curved cannula along the curved path to provide access to the spine proximate the target location; and
sliding a bore of a second curved cannula over the curved guide member along the curved path such that the bore of the first curved cannula receives the second cannula as the first curved cannula moves along the curved path.

16. A method of creating an initial pathway to a targeted portion of a patient's spine, the method comprising:
advancing a distal tip of a targeting post into a patient from a starting point posterior of the patient;
placing the distal tip of the targeting post at a reference location;
connecting a proximal end of the targeting post to an instrument support arm which is stabilized to stabilize the targeting post;
connecting a proximal end of a curved penetrating guide member to a distal end of a guide arm to form a rigid but reversible connection;
connecting a proximal end of the guide arm to the proximal end of the targeting post to form a rotatable connection;
rotating the guide arm and the curved penetrating guide member relative to the rotatable connection to move a distal end of the curved penetrating guide member to a target location offset from the reference location, the rotation of the curved penetrating guide member in a plane that does not include the distal tip of the targeting post;
disconnecting the proximal end of the curved penetrating guide member from the distal end of the guide arm;
inserting a distal end of a first curved cannula over the proximal end of the curved penetrating guide member; and
sliding the first curved cannula along the curved path from the proximal end of the curved penetrating guide member toward the distal end of the curved guide member.

17. The method of claim 16 where the reference location that receives the distal tip of the targeting post is not within a vertebra.

18. The method of claim 16 where the reference location that receives the distal tip of the targeting post is not part of a targeted intervertebral disc space.

19. The method of claim 16 wherein the distal tip of the targeting post is placed at a reference location coplanar with a superior endplate of an inferior vertebral body for an intervertebral disc space to receive therapy.

20. The method of claim 19 wherein the distal tip of the targeting post is placed at a reference location at an anterior lateral half of an intervertebral disc space to receive therapy.

21. The method of claim 19 wherein the distal tip of the targeting post is placed at a reference location at an anterior lateral third of an intervertebral disc space to receive therapy.

22. The method of claim 16 wherein the step of advancing the distal dip of the targeting post uses a neural monitoring system to detect nerves in proximity to the distal tip of the targeting post.

23. The method of claim 22 wherein the step of rotating the guide arm and the curved penetrating guide member uses a neural monitoring system to detect nerves in proximity to a distal end of the curved penetrating guide member.

24. The method of claim 16 wherein the distal end of the targeting post penetrates muscle and fascia.

25. The method of claim 16 wherein the distal end of the curved penetrating guide member penetrates soft tissue and fascia of the patient as the distal end is advanced to the target location.

26. The method of claim 16 wherein the targeting post is positioned to be co-planar with a superior endplate of an inferior vertebral body adjacent a targeted intervertebral disc space.

27. The method of claim 16 wherein the targeting post is positioned to be parallel to a medial-sagittal plane of the patient.

28. The method of claim 16 wherein the targeting post has a cephalad-caudal adjustment which is adjusted while the distal tip of the targeting post is at the reference location to adjust an offset between the plane that contains the rotation of the curved penetrating guide member and the distal end of the targeting post.

29. The method of claim 16, further comprising withdrawing the curved guide member through a proximal end the first curved cannula.

* * * * *